United States Patent
Fuseri et al.

(10) Patent No.: US 7,270,671 B2
(45) Date of Patent: Sep. 18, 2007

(54) SEMI-AUTOMATIC SUTURE DEVICE FOR USING SURGICAL THREAD

(75) Inventors: Jean Fuseri, La Destrousse (FR); Yves Alimi, Marseille (FR); Frédéreic Mouret, Marseille (FR); Vincent Garitey, Marseille (FR); Régis Rieu, Marseille (FR)

(73) Assignees: Unversite de la Mediterranee (Aix-Marseille II), Marseille Cedex (FR); Centre Nationale de la Recherche Scientifique (CNRS), Paris Cedex (FR)

( * ) Notice: Subject to any disclaimer, the term of this patent is extended or adjusted under 35 U.S.C. 154(b) by 2 days.

(21) Appl. No.: 10/521,966
(22) PCT Filed: Aug. 5, 2003
(86) PCT No.: PCT/FR03/02459

§ 371 (c)(1),
(2), (4) Date: Jun. 7, 2005

(87) PCT Pub. No.: WO2004/014235
PCT Pub. Date: Feb. 19, 2004

(65) Prior Publication Data
US 2005/0240203 A1 Oct. 27, 2005

(30) Foreign Application Priority Data
Aug. 6, 2002 (FR) .................................. 02 09972

(51) Int. Cl.
*A61B 17/04* (2006.01)
(52) U.S. Cl. ................. 606/148; 606/144; 606/232
(58) Field of Classification Search ........ 606/144–150, 606/228–233, 139, 213–216, 221; 112/254, 112/59
See application file for complete search history.

(56) References Cited

U.S. PATENT DOCUMENTS

| | | | | |
|---|---|---|---|---|
| 3,766,925 A | * | 10/1973 | Rubricius | .................... 606/120 |
| 3,931,821 A | | 1/1976 | Kletschka et al. | |
| 5,222,974 A | * | 6/1993 | Kensey et al. | .............. 606/213 |
| 5,356,459 A | | 10/1994 | Bikson et al. | |
| 5,474,572 A | * | 12/1995 | Hayhurst | ..................... 606/232 |
| 5,669,917 A | | 9/1997 | Sauer et al. | |
| 5,911,728 A | | 6/1999 | Sepetka et al. | |
| 6,066,160 A | | 5/2000 | Colvin et al. | |
| 6,077,277 A | | 6/2000 | Mollenauer et al. | |

(Continued)

FOREIGN PATENT DOCUMENTS

FR 2628964 9/1989

*Primary Examiner*—Glenn K. Dawson
*Assistant Examiner*—Kathleen Sonnett
(74) *Attorney, Agent, or Firm*—Young & Thompson

(57) ABSTRACT

The present invention provides an implantable device for semiautomatic suturing using a surgical thread, the suturing enabling biological and/or artificial tissues to be united, the device comprising: blocking means enabling two strands of the thread of a suture to be connected together in a blocking zone; a bearing element having a bearing surface for bearing against the tissues to be sutured together; and controlled tensioning means for applying controlled tensioning to said thread, and suitable, after the two strands of said thread have been blocked together using said blocking means, for exerting a tension at a first predetermined tension value, with the junction between said bearing element and said blocking zone of the device being provided by said controlled tensioning means.

21 Claims, 10 Drawing Sheets

U.S. PATENT DOCUMENTS

| | | |
|---|---|---|
| 6,159,234 A | 12/2000 | Bonutti et al. |
| 6,174,324 B1 * | 1/2001 | Egan et al. ............... 606/232 |
| 6,217,591 B1 | 4/2001 | Egan et al. |
| 6,241,749 B1 | 6/2001 | Rayhanabad |
| 6,293,961 B2 | 9/2001 | Schwartz et al. |
| 6,368,326 B1 * | 4/2002 | Dakin et al. ............... 606/103 |

* cited by examiner

SEMI-AUTOMATIC SUTURE DEVICE FOR USING SURGICAL THREAD

This application is a filing under 35 USC 371 of PCT/ER2003/02459 filed Aug. 5, 2003.

The present invention relates to a semiautomatic implantable surgical device for suturing with surgical thread. More particularly, the present invention relates to a suture device including blocking means for blocking together two strands of thread in a suture.

The present invention relates still more particularly to a device for suturing by a minimally invasive surgical approach. Minimally invasive surgery consists in making cutaneous and parietal incisions of small size and introducing instruments and viewing means such as a camera in order to perform an operation in video-assisted manner through orifices having a diameter lying in the range 3 millimeters (mm) to 12 mm by means of a hollow cylindrical instrument referred to as a "trocar".

BACKGROUND OF THE INVENTION

In minimally invasive surgery, anastomoses are often made using sutures of surgical thread secured by knots. Tying a knot on an organ or a vessel constitutes a difficult step during surgery since:

any slackening of sutures can lead to complications that are severe or even fatal;
  tying knots while using a laparoscopic approach is technically difficult; and
  the increasing number of knots required increases the duration of surgery in significant manner, and for certain operations, such as those involving vascular clamping where operating time must be kept very short, that can run the risk of leading to operative or postoperative complications.

Proposals have been made to use clip or staple type devices, in particular in U.S. Pat. No. 5,356,459 which seeks to replace suture thread in order to avoid the need to tie knots. Nevertheless, surgeons prefer to use thread when suturing, since they have acquired automatic and habitual skills such that the sutures they make in this way are tried and tested. In addition, the reliability of clip or staple type devices has yet to be validated.

OBJECTS AND SUMMARY OF THE INVENTION

That is why the present invention seeks to provide a device for suturing using a thread, but offering an alternative to tying knots so as to make it easier to connect two strands of suture thread together, and making it possible significantly to reduce the time required for connecting said strands of thread together.

The inventors have discovered that one of the difficulties in tying knots in suture thread lies in the need for the surgeon to exert tension on the thread, firstly in order to tighten the suture prior to making a permanent connection between the two strands of thread, and secondly to make it easier to tie the knot. One difficulty thus lies in the need for the surgeon to control the tension to be exerted on the thread in order to avoid tightening excessively, or conversely tightening insufficiently, which in both cases would lead to a suture that is ineffective. Controlling thread tension and tying the knots themselves are both acts that are difficult since they need to be done using forceps that are long (20 centimeters (cm) to 30 cm), through trocars, and in a space that is confined. Excessively tightening the threads can lead to a thread itself breaking or to pinching of the biological tissue that is to be repaired. Such pinching can lead to phenomena of tissue rupture or of inflammatory reaction. In contrast, when tightening is not sufficient, the junction between pieces of tissue or between a tissue and a prosthesis can be imperfect and the suture is not leaktight.

U.S. Pat. Nos. 5,669,917, 6,066,160, 6,077,277, 6,217,591, and 6,293,961 propose various devices enabling two strands of thread to be connected and blocked together instead of requiring the surgeon to tie knots. Nevertheless, in those prior devices, it is always necessary to put the thread under tension in order to tighten the suture before connecting and blocking together the two strands of thread. During this step, it is not possible for the tension exerted on the thread by the surgeon to be controlled automatically in any way.

In addition, in some of the proposed devices, the suture that is made cannot be easily undone, should that be necessary.

The object of the present invention is thus to provide a surgical suture device that is compatible with using conventional suture thread so as to conserve the benefits of conventional surgery and increase the confidence of the surgeon, while remedying the drawbacks of prior devices.

In particular, an object of the present invention is to provide a suture device that makes it possible to block suture threads quickly and reliably in a manner that is semiautomatic for the surgeon.

Another object of the present invention is to provide a suture device such that the suture made thereby is of reversible or removable character, and in particular can be cut almost instantaneously without any risk of damaging the surrounding tissues.

For this purpose, the present invention provides a suture device comprising: blocking means for connecting together two strands of thread in a blocking zone; and controlled tensioning means for controlled tensioning of said thread, and suitable, after the two strands of said thread have been blocked together using said blocking means, for exerting tension on the thread at a first predetermined tension value.

More precisely, the present invention provides an implantable device for semiautomatic suturing using a surgical thread, the suturing enabling biological and/or artificial tissues to be united, the device comprising: blocking means enabling two strands of the thread of a suture to be connected together in a blocking zone; a bearing element having a bearing surface for bearing against the tissues to be sutured together; and controlled tensioning means for applying controlled tensioning to said thread, and suitable, after the two strands of said thread have been blocked together using said blocking means, for exerting a tension at a first predetermined tension value, with the junction between said bearing element and said blocking zone of the device being provided by said controlled tensioning means.

Two strands of thread are said herein to be "connected together" when the two strands cannot move relative to each other in said blocking zone, i.e. they are not necessarily in contact with each other in said blocking zone.

The device can be used to unite pieces of biological tissue, one or more pieces of biological tissue with one or more pieces of artificial tissue, or solely pieces of artificial tissue.

In the device of the invention, said blocking means and said tensioning means are suitable for co-operating so that two strands of suture thread are blocked together before exerting said first predetermined tension value, and once the two strands have been blocked together, the device tensions the suture threads at said first predetermined tension value in automatic manner.

Tensioning said suture thread enables the two pieces of tissue, or a piece of tissue and a prosthesis, that are to be united by said suture to be moved together effectively by tightening the thread. With prostheses, said tissue can be biological or artificial.

The term "controlled tensioning" is used herein to mean tensioning at a said first known and predetermined tension value, which tensioning can be applied automatically using said tensioning means, and no longer depends on the initial tension exerted manually by the surgeon on the thread or on a device; that is why the device of the invention is said to be "semiautomatic".

The fact of tensioning the suture threads to a said first predetermined tension value in controlled manner gives the device dynamometric behavior and contributes to the effectiveness of the device and the speed and ease of suturing using the device. The dynamometric behavior of the device of the invention serves to ensure that tensioning is applied appropriately, uniformly, reliably, and repetitively on the threads that are to constitute the suture. Having tension that is uniform makes it possible to distribute forces evenly over the sutured tissues, and thus to minimize aggression to said tissues.

Said first predetermined tension value may preferably lie in the range 0.1 newtons (N) to 10 N, depending on the site of surgery, i.e. depending on the type of tissue to be sutured and depending on the type of suture thread used, and in particular it may be about 2 N which corresponds to the mean tension value of a suture made between a vessel and a vascular prosthesis during conventional surgery under good operating conditions.

In a preferred embodiment, the blocking of said strands of thread using said blocking means is suitable for automatically triggering said tensioning of the thread at a said first predetermined tension value, preferably lying in the range 0.1 N to 10 N.

More particularly, in a dynamometric suture device of the invention, said controlled tensioning means are suitable for co-operating with:
  a bearing element having a bearing surface for bearing against said tissue to be sutured in a zone ($4_1$) where the device contacts said tissue; preferably in the proximity of suture orifices in said tissue; and
  said blocking means (2) in such a manner as to enable the distance between said blocking zone and said zone of contact between the device and the tissue to be adjusted between:
    an initial distance (L) in which said blocking of the two ends of the strands of thread can be performed with the thread being at a tension that is preferably small; and
    a final distance (L'=L±b) suitable for exerting a said controlled tension at a said first predetermined tensioning value.

Thus, if the tension exerted by the surgeon on the thread prior to blocking is less than said first predetermined tension value, then said final distance (L+b) will be longer than said initial distance, and conversely if the tension exerted on the thread by the surgeon prior to blocking is greater than said predetermined tension, then said final distance (L−b) will be shorter than said initial distance.

Still more particularly, in a suture device of the invention, said tensioning means for adjusting the distance between a said zone of contact on said tissue and said blocking zone, comprise said junction means between said contact zone and said blocking zone.

Said first controlled tension value is thus achieved by adjusting the distance between two zones, namely a contact zone and a blocking zone, by means of a junction element, which adjustment is a function both of said initial distance between said two zones and of the initial tension of the thread as exerted by the surgeon prior to blocking.

As mentioned above, tensioning the threads, and thus implementing said adjusted distance between the contact zone and the blocking zone, is preferably triggered automatically by causing said thread blocking means to operate. Nevertheless, such triggering can be implemented manually by the operator, particularly by relaxing a pressure being exerted by the operator for maintaining said initial pressure manually.

The device of the invention is advantageously put into contact with the tissue to be sutured by means of a placing instrument known as an "ancillary". The suture device of the invention is thus suitable for co-operating with said placing instrument to which it is secured prior to said blocking, preferably being secured via a top portion corresponding to said blocking zone, and, where appropriate, tensioning of the thread after blocking may be triggered manually using said placing instrument.

In an embodiment, the placing instrument may also serve to cut the ends of the strands of suture thread over the thread blocking zone at a distance lying in the range 1 mm to 10 mm, and in particular 5 mm to 6 mm from the blocking zone, after the threads have been blocked together and depending on the anatomic site of the surgery.

In a preferred embodiment, said tensioning means comprise means for establishing a resilient junction between said contact zone and said blocking zone so as to enable the distance to be adjusted between:
  a controlled initial distance (L) in which the spacing between said contact zone and said blocking zone is controlled by a first link element or a first spacer element, with said initial distance (L) corresponding to a distance in which said blocking zone and contact zone are in a close position obtained by compression from a remote, rest position (L+a); and
  said final adjusted distance (L'=L±b, b<a) which corresponds to a force equilibrium position in which the distance between said contact zone and said blocking zone is no longer controlled by a said first link element or a said first spacer element.

The term "force equilibrium" is used herein to mean equilibrium between the force exerted by the junction means and the tension of the suture.

Said first link element and/or said first spacer element may be secured to said placing instrument or to said suture device proper.

More particularly, said junction means are made of a material that presents elasticity, and said suture device is secured to the placing instrument via said blocking zone such that:
  when pressure is exerted on said blocking zone, it is possible, where appropriate, to move said blocking zone from the natural, rest position (L+a) of the device to said initial distance (L), in which said blocking together of the two strands of thread can be implemented under arbitrary tension as exerted on the suture thread by the surgeon, and preferably under no tension; and said tensioning of the suture thread exerted by the device of the invention takes place after said blocking by returning said blocking zone to a said adjusted final distance (L±b) on releasing the pressure exerted on said blocking zone.

The blocking zone and the contact zone can be brought towards each other to said initial distance (L) even before the threads are inserted into the device. The device is then pre-stressed when in position in its placing instrument.

In a first variant embodiment, said initial distance may be obtained using a first link element such as a tab suitable for initially connecting said blocking zone and said tissue contact zone, and said adjusted final distance of said blocking zone relative to said contact zone can be implemented by releasing said first link element connecting together said blocking zone and said contact zone of the device.

Preferably, said first link element forms a part of said suture device of the invention, and release of said link element can be triggered manually, in particular using the instrument for placing the device of the invention, or else it can be triggered automatically, if said first link element is also connected to said blocking means in such a manner as to release first link element once said blocking means have been locked.

That is why, in a preferred embodiment, said first link element is suitable for co-operating with said blocking means so that said first link element is released once said strands of thread have been blocked together with the help of said blocking means.

In a second variant embodiment of the invention, the device includes resilient junction means and it is suitable for co-operating with a placing instrument to which it is preferably secured via a top portion corresponding to said blocking zone, such that:

prior to said contact zone coming into contact with said tissue, said resilient junction means are at rest and said contact zone and said blocking zone are in the remote position (L+a);

when said contact zone is caused to exert pressure on said tissue to be sutured, said resilient junction means are in compression and the distance between said blocking zone and said contact zone decreases down to a said initial distance (L) as controlled by a said minimum spacer element, which element is preferably secured to said placing instrument, said bearing contact zone coming into abutment against said spacer element of said placing instrument; and said final distance (L±b, b<a) is obtained by co-operation between said spacing instrument and said device, preferably by separating said placing instrument from said suture device.

The term "resilient junction means at rest" is used to mean that said resilient means are not under stress.

More particularly, said junction means are made of a material that presents elasticity, and the displacement of said blocking zone and said contact zone is controlled by the placing instrument which is secured to said blocking zone in such a manner that:

when pressure is exerted on said blocking zone, said blocking zone can be moved from a remote position (L+a) to a first close position (L) corresponding to said initial distance, in abutment against said first spacer element of said placing instrument, in which it is possible to block the two strands of thread together under arbitrary tension exerted by the surgeon, which tension may be greater than or less than said first predetermined tension value; and the suture thread is tensioned after said blocking and after the placing instrument has been withdrawn, when the pressure exerted on said blocking zone is released by moving said blocking zone towards a second adjusted position (L±b), which position may be closer (L−b) than said first position if the tension exerted on the thread by the surgeon was greater than said predetermined tension value, or it may be further away (L+b) than said first position if the tension exerted on the thread by the surgeon was less than said predetermined tension value.

According to another advantageous characteristic of the device of the invention, it is of a shape such that after suturing has been performed, the thread is unencumbered so as to be capable of being cut between said blocking zone and said suture orifices in said tissue, and preferably between said blocking zone and said contact zone.

This makes it easier to cut the threads, and also to eliminate the suture should that be necessary. The reversible nature of the suturing performed by the device makes it possible, in the event of wrong positioning, to return to a preceding situation almost instantaneously, thus giving the surgeon greater freedom of choice and freedom of action throughout the time surgery is taking place.

According to another advantageous characteristic of the device of the invention, it includes guide means enabling the two strands of thread to be held in a position where they are spaced apart from each other laterally at the suture orifices in said tissue.

Said guide means are more particularly suitable for maintaining the two threads in a spaced-apart position when tension is exerted on said thread after the strands of thread have been connected together at said blocking zone by said blocking means. It will be understood that said guide means then make it possible to avoid tearing the tissue at the orifices where the thread passes through said tissue when tension is exerted on the thread after the ends of the thread have been blocked together.

More particularly, the device of the invention has said guide means at said thrust surface defining said zone of contact between the device and the tissue.

In a preferred embodiment of the invention, said guide means comprise at least one notch formed in said bearing surface defining said contact zone.

Also preferably, beneath a said notch, said bearing surface has a piece of fabric made of biocompatible materials and suitable for having two strands of thread pass therethrough, and suitable for keeping them spaced apart. The fabric may be constituted in particular by a synthetic material that facilitates hemostasis and that preserves the integrity of the biological or synthetic tissues to be sutured. In particular, it an be constituted by a piece of vascular prosthesis, a compress, or a swab.

In the conventional technique for maintaining lateral spacing between the orifices in a conventional suture, the surgeon uses a "pledget". This is a piece of fabric, in particular made of Dacron® or Teflon®, through which the surgeon passes the two strands of thread separately, and it acts as an intermediary between the knots and the tissue to be sutured.

In the invention, the covering of biocompatible material acting as means for guiding and separating the strands of the suture thread where they leave the sutured tissues also acts as a traditional pledget, but it is integrated in the device, thereby making contact between the device and the tissue gentler and less traumatic, and performing the pledget function of facilitating hemostasis and preserving the integrity of the sutured tissues.

In a preferred embodiment, said blocking means comprise two blocking surfaces which can move between a spaced-apart position in which it is possible to insert said strands of suture thread between said two blocking surfaces, and which is suitable for blocking the strands of thread together by friction between the threads and said two blocking surfaces once the surfaces are in the close-together, blocking position, with the displacement of said two blocking surfaces between said spaced-apart position and said close-together position preferably automatically triggering said tensioning of the threads.

It is advantageous for the suture threads to be blocked together by a friction force rather than by a pinching force which would imply a risk of the threads breaking. For this purpose, said blocking surfaces need to present the following characteristics:

the material used for making the blocking surfaces must be compatible with the material constituting the suture threads;

the surfaces must be as large as possible in order to maximize contact area with the threads, thereby increasing the friction force; and the surfaces must not present sharp angles that might cut the thread.

In a preferred embodiment of the device of the invention, said blocking of the strands of thread using said blocking means is suitable for being triggered automatically.

Automatic triggering of the blocking mechanism can take place via the instrument that is used for inserting and placing the device of the invention at the suture.

More particularly, the automatic triggering of said blocking means can take place when the device of the invention is put into contact with the tissues for suturing with a bearing force that is greater than a second predetermined value lying in the range 0.2 N to 20 N, and in particular greater than 10 N. This bearing force estimated at 10 N corresponds to the force developed by a surgeon when pulling on the suture threads while making a first knot in a traditional suture for performing anastomosis of the abdominal aorta. The magnitude of this bearing force naturally varies with the type of surgery being performed and with the type of suture thread being used.

Advantageously, said blocking means comprise two jaws that are elastically connected together and that form said blocking surfaces, which jaws are spaced apart by a second spacer element, and said second spacer element is suitable for being released by being disengaged or by being broken, thereby allowing said blocking surfaces to move towards each other and block said strands of thread.

Said second spacer element may be an element of said suture device itself, or of said placing instrument.

More particularly, said second spacer element is suitable for being released automatically, preferably by said placing instrument pressing against said second spacer element, whenever said bearing surface of the device exerts pressure on the tissues that is greater than a said second predetermined value preferably lying in the range 0.2 N to 20 N, and more preferably of at least 10 N.

Still more particularly, said second spacer element is suitable for being released by automatically triggering the release of said first link element between said blocking zone and said contact zone of the device so that said zones adopt said adjusted final distance that enables a said control tension to be exerted on said thread.

In an advantageous embodiment of the present invention, the bearing force exerted at the base of the device of the invention against the tissues enables said second spacer element to be released, thereby preferably triggering tensioning of the thread after said strands of thread have been blocked, tensioning being at a said first tension value, by releasing, where appropriate, said first link element for maintaining the fixed spacing between said blocking zone and said contact zone at said initial distance, so that said blocking and contact zones adopt a said adjusted distance.

In another embodiment, said blocking means comprise projecting elements that are preferably of circular section, more preferably of cylindrical shape, having the ends of the strands of thread for connection together wound thereabout. More particularly, said blocking can be achieved by moving said projecting elements towards each other or away from each other.

In another embodiment, said blocking means include a blocking orifice in said blocking zone, said blocking orifice co-operating with a second blocking element comprising a screw, a rivet, a pushbutton, or indeed a jam cleat.

In another embodiment, said blocking means comprise means for sticking, melting, heat-sealing, or crimping the two strands of thread together in a said blocking zone.

Preferably, the blocking between said strands of thread must be capable of withstanding a traction force lying in the range 0.5 N to 50 N, and in particular of about 20 N to 30 N, with the suture thread breaking at a higher force.

If the shape of the device of the invention, and if particular of said junction element between said bearing surface and said blocking zone, does not make it possible to provide access for cutting the threads in order to undo the suture and remove the device, an alternative is to provide blocking means in such a manner that the blocking means can be unlocked with an instrument, thereby releasing the threads from being blocked together.

In the present invention, the term "implantable device" is used to mean a device of size and of biocompatible constituent materials that enable it to be implanted in the human body, and more particularly implanted for the long term, inside the human body, i.e. for a duration of more than 30 days.

Similarly, in the present invention, the term "implantable by a minimally invasive approach" is used to mean that the device of the invention is sufficiently small to enable it to be implanted by a minimally invasive approach, and more particularly through a trocar, in particular a trocar having a diameter lying in the range 2 mm to 20 mm. Still more particularly, the device of the invention presents dimensions in terms of height and width that lie in the range 2 mm to 20 mm, and preferably in the range 5 mm to 10 mm.

A device of the invention can be used in minimally invasive surgery, in particular in robot-assisted surgery, and also in conventional surgery. Depending on the degree of miniaturization of the device, use thereof can be envisaged in various types of minimally invasive surgery, such as, for example:

abdominal surgery;

cardiothoracic surgery; and cervical surgery.

In a more advantageous embodiment, the device of the invention presents a mechanical structure that is simple and comprises, at least in part, and preferably completely, said bearing element, said blocking means, and said controlled tensioning means, forming a single integrally-formed mechanical part.

As mentioned above, the material constituting the elements making up the device of the invention is a biocompatible material. Materials of this type can be metals, plastics, or composites, and are known to the person skilled in the art. Some are given by way of example in the detailed description below.

BRIEF DESCRIPTION OF THE DRAWINGS

Other characteristics and advantages of the present invention appear in the light of the following detailed description of embodiments given with reference to FIGS. 1 to 11, in which:

In FIG. 2, the device is shown at the moment the ancillary presses against the top portion of the device immediately prior to the threads being blocked together. In FIG. 3, the device is shown while blocking is taking place. In FIG. 4, the ancillary 12 has been removed and the suture device 11 is shown after blocking has taken place.

In FIG. 5, the device is shown held in place in its placing ancillary 12. Said ancillary is shown in face view in FIG. 6 and in side view in FIG. 7.

In FIGS. 1-3 and 5-7, said ancillary is shown purely diagrammatically, and only the bottom portion thereof that co-operates with the device.

In FIGS. 1 to 11, the suture device of the invention is shown diagrammatically so as to present its various component elements more clearly.

MORE DETAILED DESCRIPTION

Figure 1:
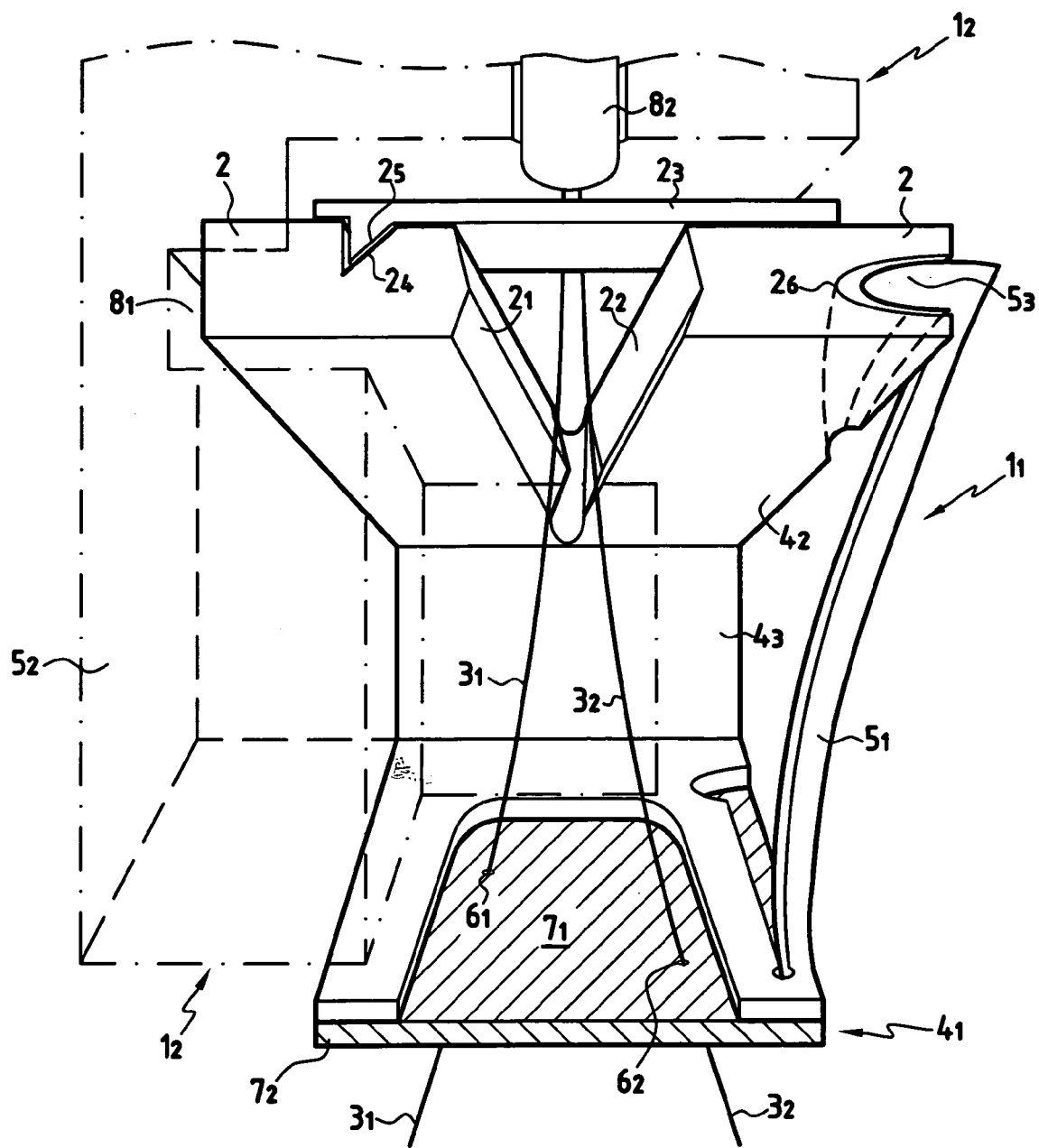
FIGS. 1 to 4 show a first variant embodiment of a U-shaped suture device of the invention, with the device being shown in FIG. 1 held stationary on an ancillary 12 prior to being put into place.
Figure 2:
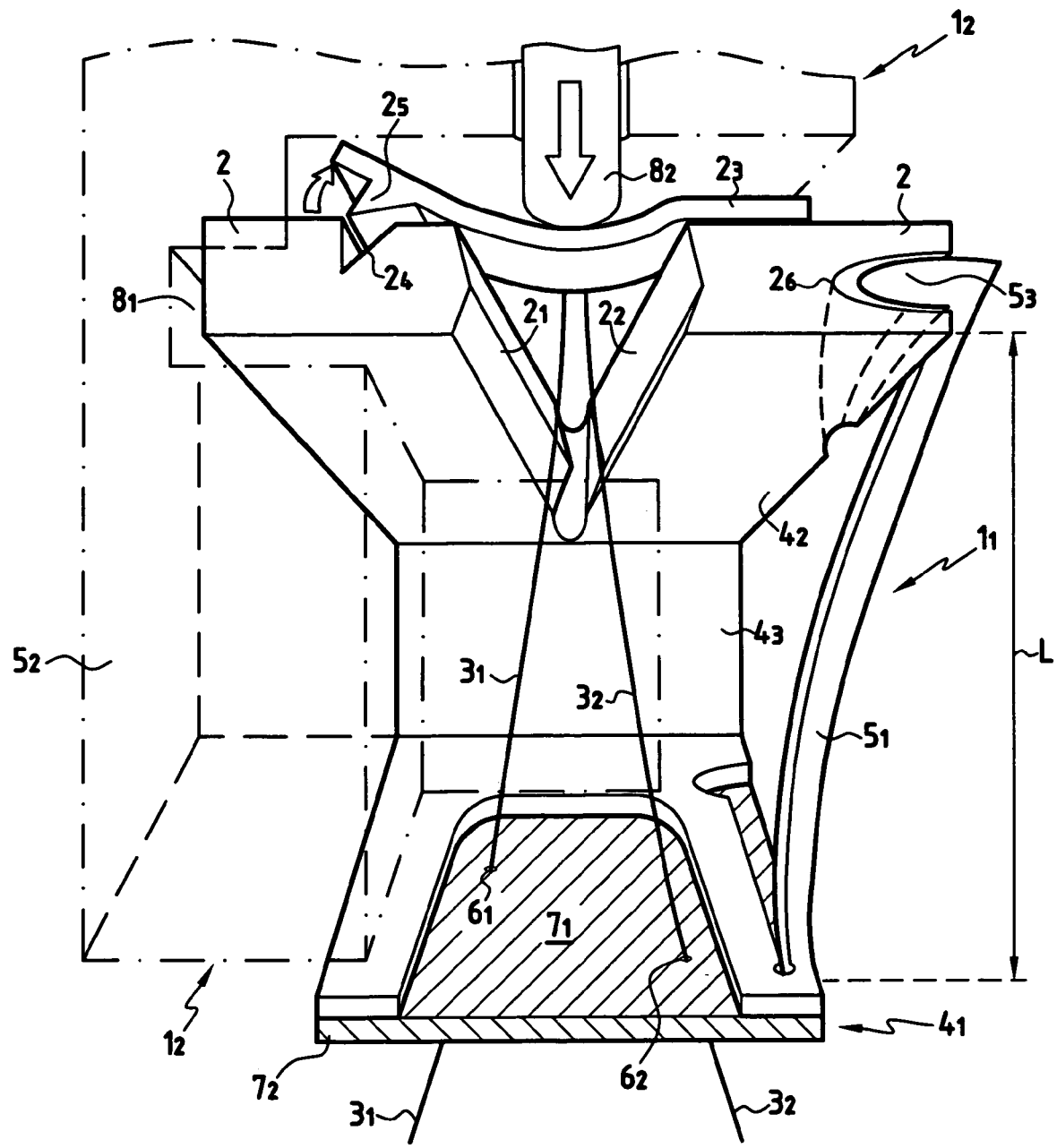

In a first variant embodiment shown in FIGS. 1 to 7, the device of the invention is U-shaped and comprises:

a bottom first branch $4_1$ defining a said bearing surface and contact zone against said tissue;

a top second branch $4_2$ comprising said blocking zone and secured to or co-operating with said blocking means 2; and a junction element $4_3$ between said first and second branches $4_1$, $4_2$ and made of a semirigid material presenting a said degree of elasticity. The junction element is straight or preferably curved so as to provide a hairpin junction between said two branches.

The entire device can be made of biocompatible materials that are metals, plastics, or composites, and in particular it can be made of 316L steel, of titanium, or of polypropylene.

In this embodiment, the space between the two branches of U has only two strands of thread passing therethrough, which strands can therefore be cut in this location, should that be necessary.

Said first tension value exerted by the device depends on a dimensional parameter, in particular on the section of the hairpin junction elements $4_3$ and on the nature of the material used. It is preferably about 2 N for an application to surgery of the abdominal aorta using threads made of polypropylene 4.0.

FIGS. 1 to 4 are diagrams showing a suture device of the invention that is U-shaped in this first embodiment described below.

The top branch $4_2$ defines a blocking zone having two jaws 2 that are initially open, i.e. spaced apart, serving to block the threads $3_1$ and $3_2$ by the threads rubbing against two adjacent and complementary surface $2_1$ and $2_2$ on respective ones of the two jaws 2 when said two complementary surfaces $2_1$ and $2_2$ close against each other with the threads thus being blocked between them.

The two jaws 2 are made of polypropylene, for example, and they are resiliently connected together, their two complementary surfaces $2_1$ and $2_2$ being initially held spaced apart by a spacer tab $2_3$. In this case, the spacer tab $2_3$ is secured to one of the jaws 2 at one end, while its other end carries a tooth $2_5$ which co-operates with a notch $2_4$ in the second jaw so that said two complementary surfaces $2_1$ and $2_2$ close against each other when said tooth $2_5$ of the tab $2_3$ is disengaged from the notch $2_4$, thereby releasing the two jaws 2.

Said complementary structures $2_1$ and $2_2$ of the two jaws 2 are preferably of curved shape, forming on their surfaces paths towards the threads that are as long as possible so as to maximize the contact areas with the threads, so that the threads are blocked by friction than rather by clamping, so as to avoid damaging the threads.

The bottom branch $4_1$ includes a central notch $7_1$, itself covered on its underside by a pledget $7_2$ made of Dacron® or Teflon® serving to hold the threads $3_1$ and $3_2$ apart at the orifices $6_1$ and $6_2$ where they leave the tissues for suturing together, the spacing between equal to 3 mm to 5 mm, for example, thereby preserving the integrity of said tissues and facilitating hemostasis.

The bottom branch $4_1$, forming the zone of contact with the tissue, is connected to the top branch forming the blocking zone $4_2$ by the resilient junction zone $4_3$ and also by a first link element or link rod $5_1$. Said link rod $5_1$ has one of its ends secured to said bottom branch $4_1$, and at its other end it carries a second tooth $5_3$ which co-operates with a second notch $2_6$ in the top branch $4_2$, said second notch $2_6$ being a lateral notch, i.e. a notch in one of the sides of the top branch $4_2$.

The suture device $1_1$ co-operates with an ancillary $1_2$ on which it is held stationary. One of the jaws 2 (or both jaws 2) of the top branch $4_2$ is (or are) held relative to the ancillary $1_2$, e.g. in a hollow housing $8_1$ in which the jaw 2 is initially fitted and/or blocked.

So long as the link rod $5_1$ is not engaged in said lateral second notch $2_6$ of the top branch $4_2$, and in the absence of any blocked thread, the top and bottom branches $4_1$ and $4_2$ are in a natural rest position in which they are spaced apart by a distance L+a.

When the link rod $5_1$ is engaged in said lateral second notch $2_6$ of the top branch, the device takes up a compressed state, and the distance between the two branches $4_1$ and $4_2$ is reduced, and corresponds to said initial distance L immediately before and during blocking.

The way in which the suture device of the invention is put into place and implemented is as follows:

1) The surgeon takes the suture device $1_1$ secured to the ancillary $1_2$ at the end of a rod of the ancillary $1_2$, and places it close to the suture zone.

2) The surgeon perforates the pledget $7_2$ in the notch $7_1$ of the bottom branch $4_1$ with the suture threads $3_1$ and $3_2$, passing through the pledget at $6_1$ and $6_2$. Passing two needles connected to the suture threads $3_1$ and $3_2$ through the pledget $7_2$ is an act that is performed habitually by surgeons and presents no difficulty. Once the threads pass through the pledget $7_2$, there is no longer any risk of the threads becoming tangled together. Furthermore, because the blocking mechanism is constituted by two jaws 2 that are held spaced apart by the spacer tabs $2_3$, it is easy to insert the thread into the blocking mechanism, i.e. into the space defined by the two spaced-apart jaws 2 and said spacer tab $2_3$.

3) Subsequently, the suture device can be lowered by the device sliding along the threads $3_1$ and $3_2$ passing through the pledget $7_2$ and the space defined between the two jaws 2 and the spacer tab $2_3$ (see FIG. 1). The threads $3_1$ and $3_2$ are then under low tension and the distance between the two branch or blocking zone $4_2$ and the bottom branch or contact zone $4_1$ corresponds to said initial distance L which is maintained by the connection rod $5_1$.

Figure 3:
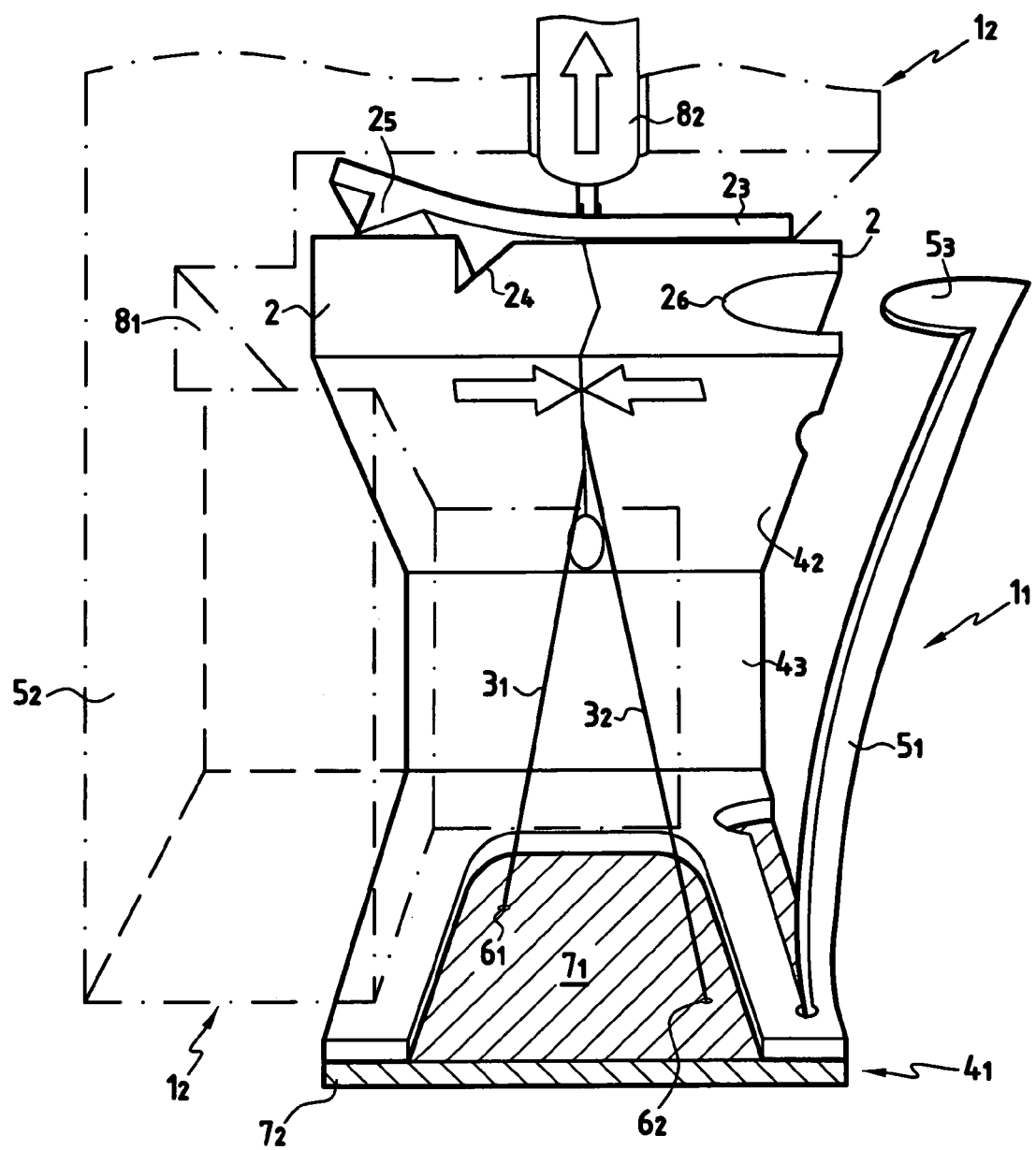
Figure 4:
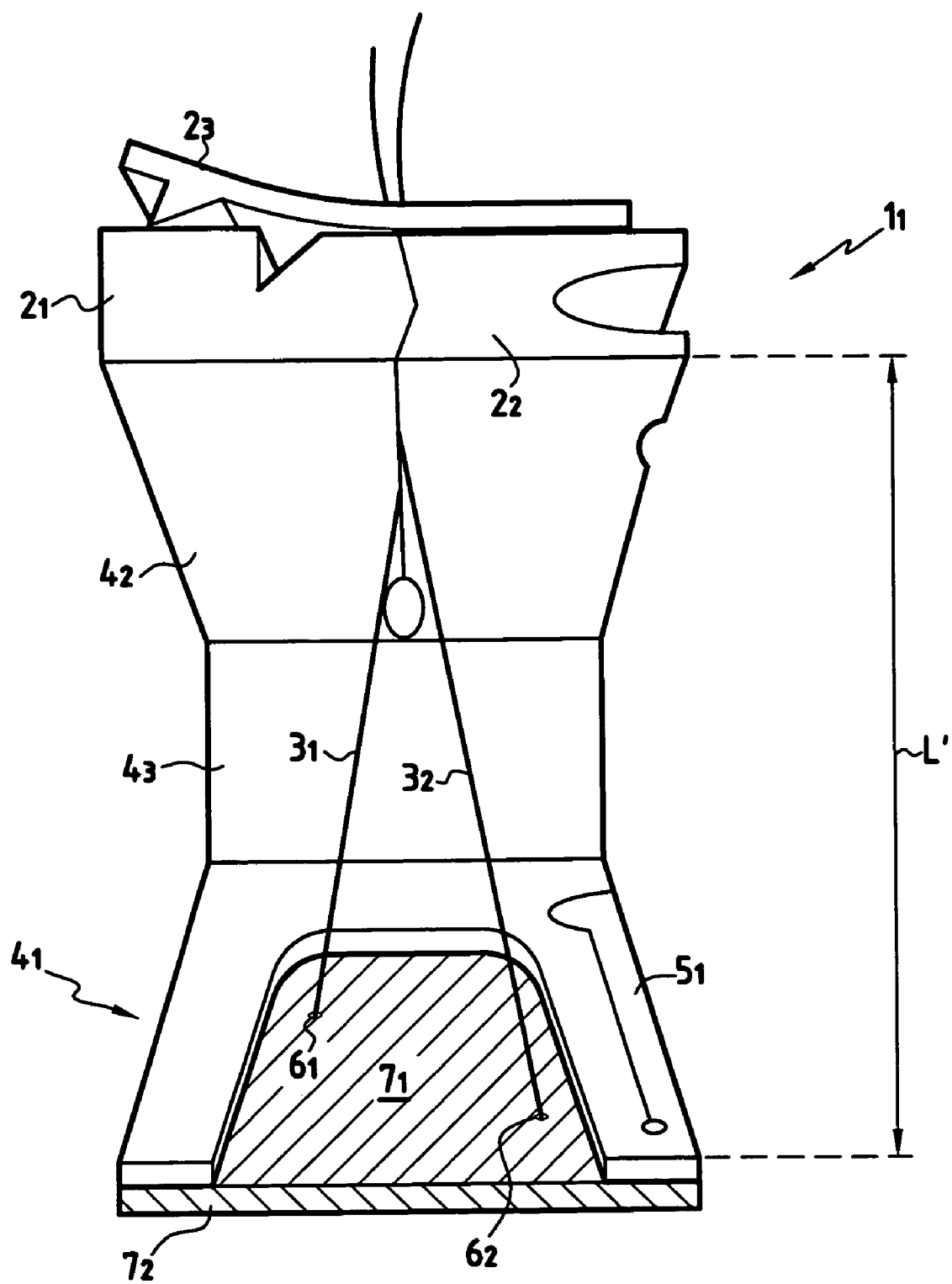

4) On coming into contact with the tissues that are to be sutured together, the surgeon presses the device $1_1$ against the tissues to be sutured by means of the placing instrument $1_2$. Once the applied thrust force reaches a predetermined level having a said second value, and in particular a value of 10 N, the pusher element $8_2$ of the ancillary provided for this purpose comes to press against the spacer tab $2_3$, thereby causing the spacer tab $2_3$ to bend in such a manner that its tooth or projection $2_5$ moves out from the notch $2_4$ (FIG. 2), thereby triggering the two resiliently interconnected jaws 2 to move towards each other and press against each other so as to block the threads $3_1$ and $3_2$ between their complementary surfaces $2_1$, $2_2$ (FIG. 3). At this stage, the threads $3_1$ and $3_2$ are blocked at a tension value that corresponds to the tension initially exerted by the surgeon on the threads while pushing the device against the tissues to be sutured together, and the distance between the contact zone of the bottom branch $4_1$ and the blocking zone of the top branch $4_2$ is L. Simultaneously, or immediately thereafter, the suture device firstly separates from the ancillary and secondly causes the link rod $5_1$ between the bottom and top branches $4_1$ and $4_2$ to become disengaged so that the distance between the top and bottom branches $4_1$ and $4_2$ can become adjusted to a said final distance L'=L±b.

The resilient junction element $4_3$ between the bottom branch $4_1$ and the top branch $4_2$ is designed in such a manner that when the distance between the bottom and top branches $4_1$ and $4_2$ is L±b with b<a, the two branches exert a tension having said first predetermined tension value, in particular lying in the range 0.1 N to 10 N, and more particularly having a value of 2 N, as explained above.

5) The threads can then be cut a few millimeters above said blocking zone $4_2$, in particular 5 mm to 6 mm above, with the threads thus being blocked together and under tension at said selected first predetermined value as obtained as a function of the way in which the suture device is made and in particular the way in which the junction element $4_3$ between the bottom and top branches $4_1$ and $4_2$ is made.

The threads $3_1$ and $3_2$ are thus blocked together automatically when the suture device comes into contact with the tissues that are to be sutured together and a bearing force is exerted on said device having a said second predetermined value, which in this case is 10 N. This value of 10 N corresponds to the force exerted by a vascular surgeon when pulling on the suture threads in order to tie a knot in a suture in the usual way. It should be observed that, prior to blocking, this initial 10 N bearing force is supported by the link rod $5_1$, which keeps the bottom and top branches $4_1$ and $4_2$ spaced apart in spite of said bearing force. Once the spacer tab $2_3$ has been disengaged and the two jaws 2 have been released, the movement towards each other of the resiliently-connected jaws 2 causes the threads to be blocked together and causes the distance between the bottom and top branches $4_1$ and $4_2$ to be come adjusted to a final distance (L±b where b<a), at which distance said branches exert a tension on the blocked-together threads, which tension has said first predetermined value.

In addition, and advantageously, the ancillary $1_2$ includes a spacer element $5_2$ which prevents the bottom branch $4_1$ with the device contact zone from moving too close to the top branch $4_2$ with the blocking zones, i.e. approaching to a distance of less than L, so that the bottom branch $4_1$ or contact zone $4_1$ can be pressed against the tissue for suturing without any risk of leading to anticipated disengagement, in particular by the link rod $5_1$ twisting.

It should be observed that the space between the bottom branch $4_1$ and the top branch $4_2$ gives access for cutting the threads $3_1$ and $3_2$, should that be necessary in order to deactivate the suture device $1_1$.

The automatic triggering of the mechanism for blocking the threads $3_1$ and $3_2$, followed by the tensioning of the blocked-together threads at a said first predetermined tension value, thus relieves the surgeon of any need to perform a whole set of acts, but without leading to any difficulty.

Figure 5:
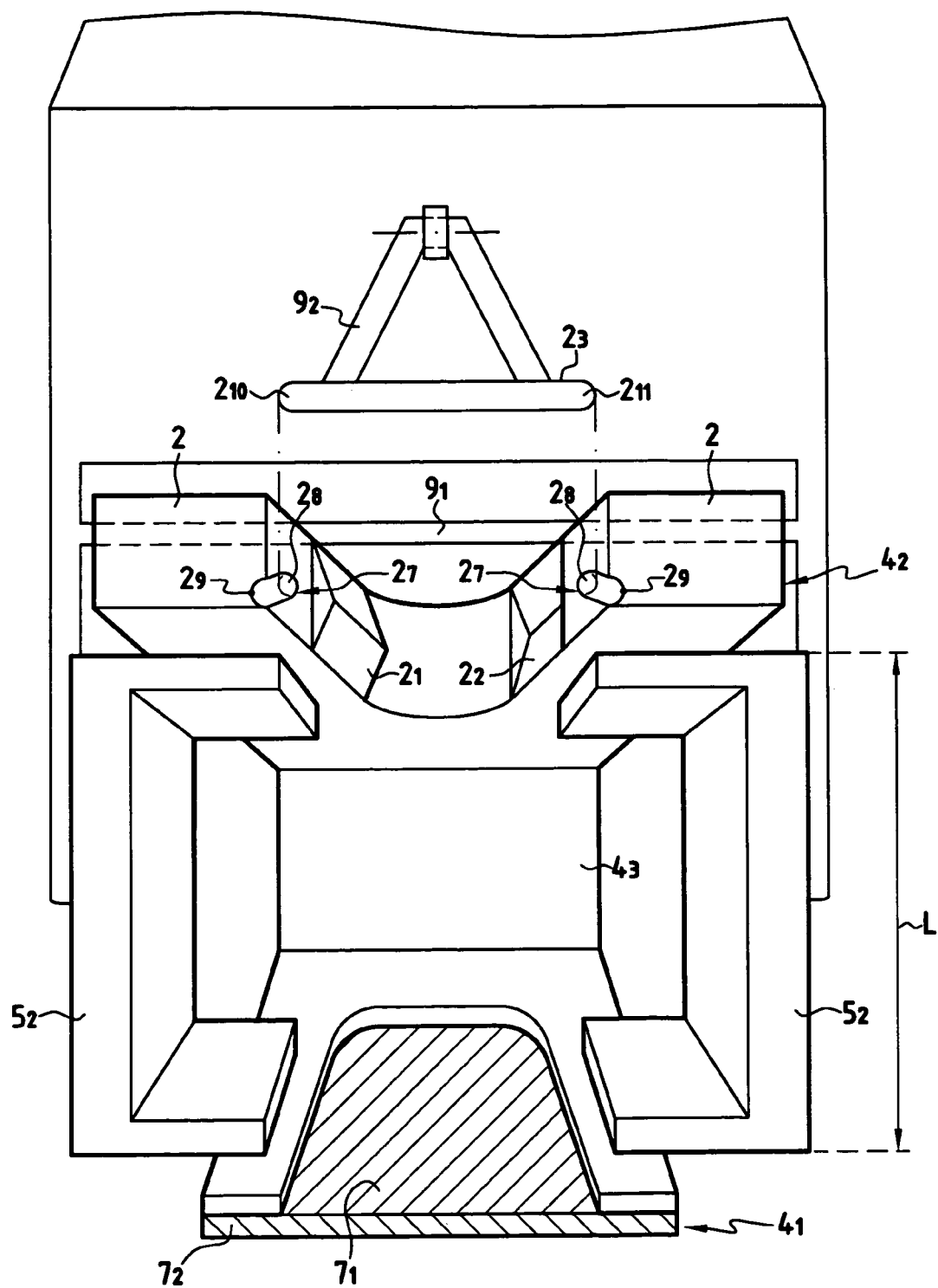
FIGS. 5 to 7 show a second variant embodiment of a U-shaped suture device.
Figure 7:
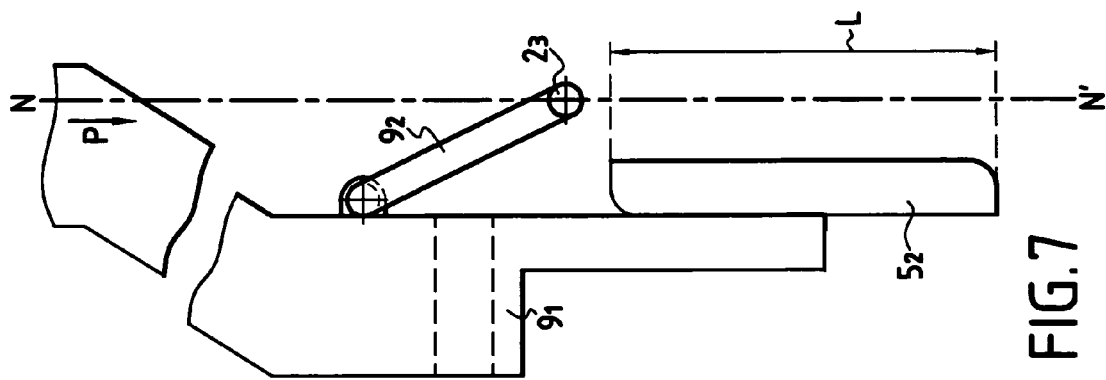
Figure 6:
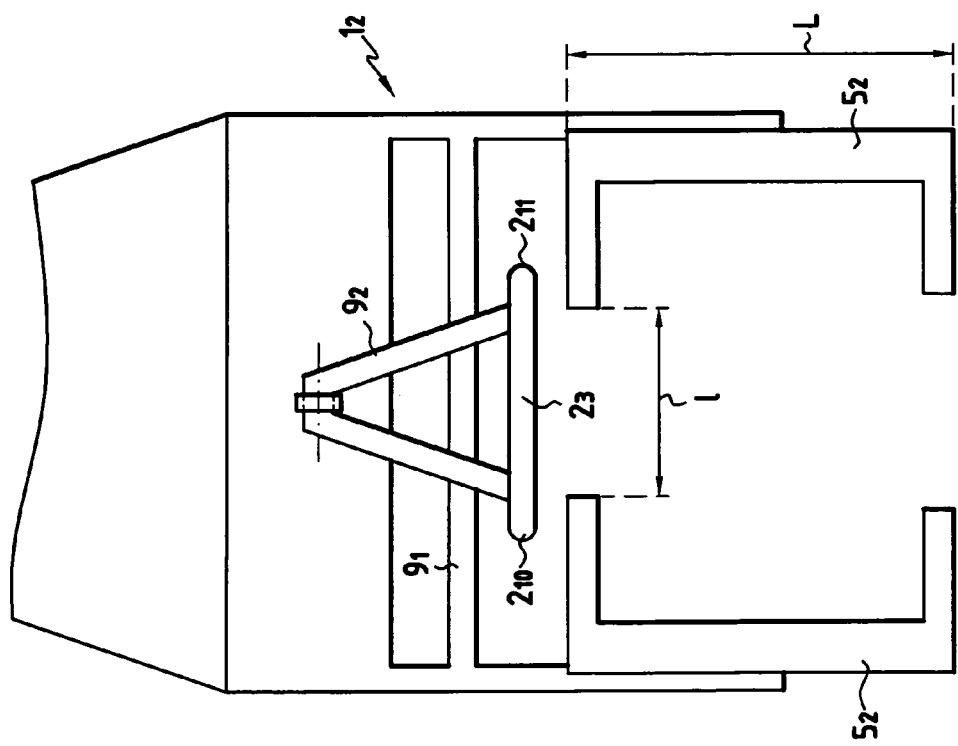

In FIGS. 5 to 7, there is shown a second embodiment of the first variant of a U-shaped suture device, which differs from the first variant as shown in FIGS. 1 to 4 as follows:

1) said second spacer element $2_3$, for spacing apart the two jaws 2 constituting said blocking zone, no longer forms a part of the suture device $1_1$ proper, but is integrated in the placing instrument $1_2$; and 2) the top and bottom branches of the U-shape respectively defining said blocking zone $4_2$ and said contact zone $4_1$ are not initially interconnected by a link rod $5_1$, but are held spaced apart by a said first spacer element $5_2$, which forms an integral portion of the placing instrument $1_2$.

As in the first variant of FIGS. 1 to 4, the suture device $1_1$ of FIGS. 5 to 7 is held stationary on the placing instrument $1_2$ via said blocking zone 2. More particularly, each of the jaws 2 is held in the spaced-apart position using the spacer bar $2_3$ of the placing instrument $1_2$, with the ends $2_{10}$ and $2_{11}$ of the bar being received in grooves $2_7$ in each of the two jaws 2. The two jaws 2 in the spaced-apart position have their bottom faces coming to bear against the top faces at the top ends of each of said two first spacer elements $5_2$ of the ancillary, and the top faces of the two jaws 2 are held by a transverse bar $9_1$ of the ancillary $1_2$.

It should be observed that initially, prior to coming into contact with the tissues to be sutured together, the bottom branch $4_1$ defining the contact zone of the device need not necessarily press against the bottom end of said spacer element $5_2$ of the ancillary. The height of said spacer element $5_2$ of the ancillary corresponds to said initial blocking distance L, such that said first spacer element $5_2$ of the ancillary $1_2$ makes it possible, when the contact zone $4_1$ of the device is brought into contact with the tissues to be sutured together, and is then pressed thereagainst, to limit the bending of the intermediate junction element $4_3$ of the device so as to maintain the distance between the blocking zone $4_2$ and the contact zone $4_1$ equal to said initial distance L. This initial distance L between the top blocking zone $4_2$ and the bottom contact zone $4_1$ corresponds to the mean value of the spacing (L±b) that needs to be maintained between these two zones of the device in order to ensure that the suture threads have said first predetermined tension value after being blocked together.

At rest, prior to being put into place, the two jaws 2 are spaced apart by the spacer rod $2_3$ of the ancillary, with the ends of the rod being received in the grooves $2_7$ in each of the two jaws 2. The grooves $2_7$ in the jaws 2 are symmetrical and designed to be of depth that varies from a deep end $2_8$ towards a shallow end $2_9$, such that:

Initially, the ends $2_{10}$ and $2_{11}$ of the spacer rod $2_3$ are received in the deep ends $2_8$ of the grooves $2_7$. In this position, the surgeon can perforate the fabric acting as the pledget $7_2$ in the notch $7_1$ with the suture threads, and can then cause the threads to pass through the space defined between the two jaws 2 and the spacer rod $2_3$ of the ancillary. The assembly can then be put into contact with the tissues to be sutured without the threads running the risk of escaping since they slide through the pledget $7_2$ and in the space defined between the two jaws 2 and the spacer rod $2_3$.

Thereafter, on coming into contact with the tissues to be sutured together, pressure P is exerted in the direction NN' on the placing instrument $1_2$, which pressure is transmitted to the spacer rod $2_3$ which is in a position such that the axis NN' passes through the middle of the rod $2_3$. As a result, the ends $2_{10}$ and $2_{11}$ of the spacer rod $2_3$ slide along the grooves $2_7$ from the deep ends $2_8$ thereof towards their shallow ends $2_9$, with the spacing between the two jaws 2 increasing.

Then, once the thrust exerted on the ancillary reaches a bearing force having a said second predetermined value, e.g. of 10 N, the jaw spacer rod $2_3$ escapes completely from the grooves $2_7$. The two jaws 2, whose complementary surfaces $2_1$ and $2_2$ are connected together resiliently, then move towards each other, thereby blocking together the suture threads $3_1$ and $3_2$. At the instant blocking takes place, the contact zone $4_1$ and the blocking zone $4_2$ constituted by the two close-together jaws 2 are spaced apart by said initial distance L corresponding to the height of said first spacer element $5_2$ of the ancillary $1_2$.

The width of the two jaws 2 after they have moved together in this way is less than the distance l between the top ends of said two first spacer elements $5_2$ of the ancillary $1_2$, so the ancillary can be withdrawn and separated from the device by being pulled upwards, the spacing between the contact zone $4_1$ and the blocking zone $4_2$ then no longer being controlled by said first spacer element $5_2$ of the ancillary $1_2$, whereupon it is said tension of said first predetermined value that is exerted by the top and bottom branches $4_1$ and $4_2$ of the device under the effect of the elasticity of the junction element $4_3$ that acts on the blocked-together threads, and in particular a said first tension value of 2 N.

Figure 8:
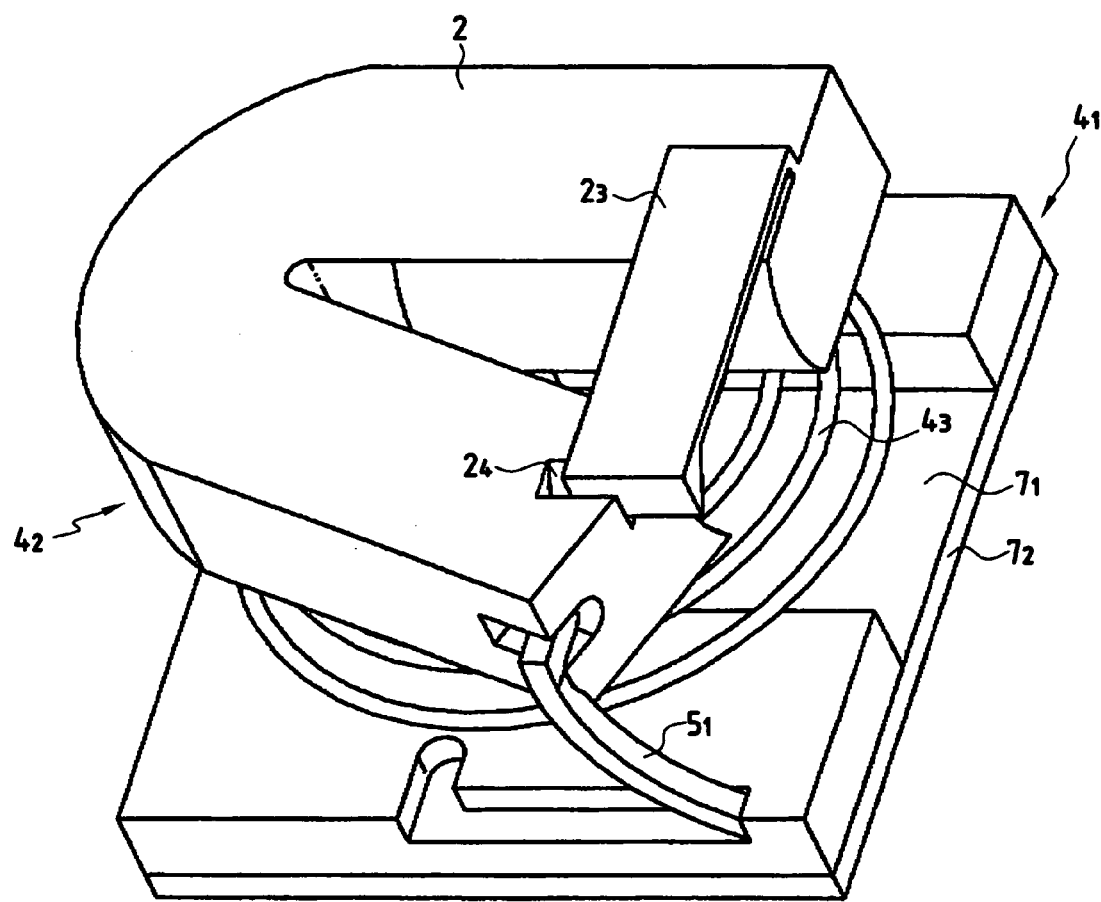
FIGS. 8 to 10 show a second variant embodiment of a suture device of the invention comprising two plates interconnected by a conical spring which is shown in its initial position prior to blocking in FIG. 8, then in its blocking position in FIG. 9, and finally in the tensioning position of the device in FIG. 10.
Figure 9:
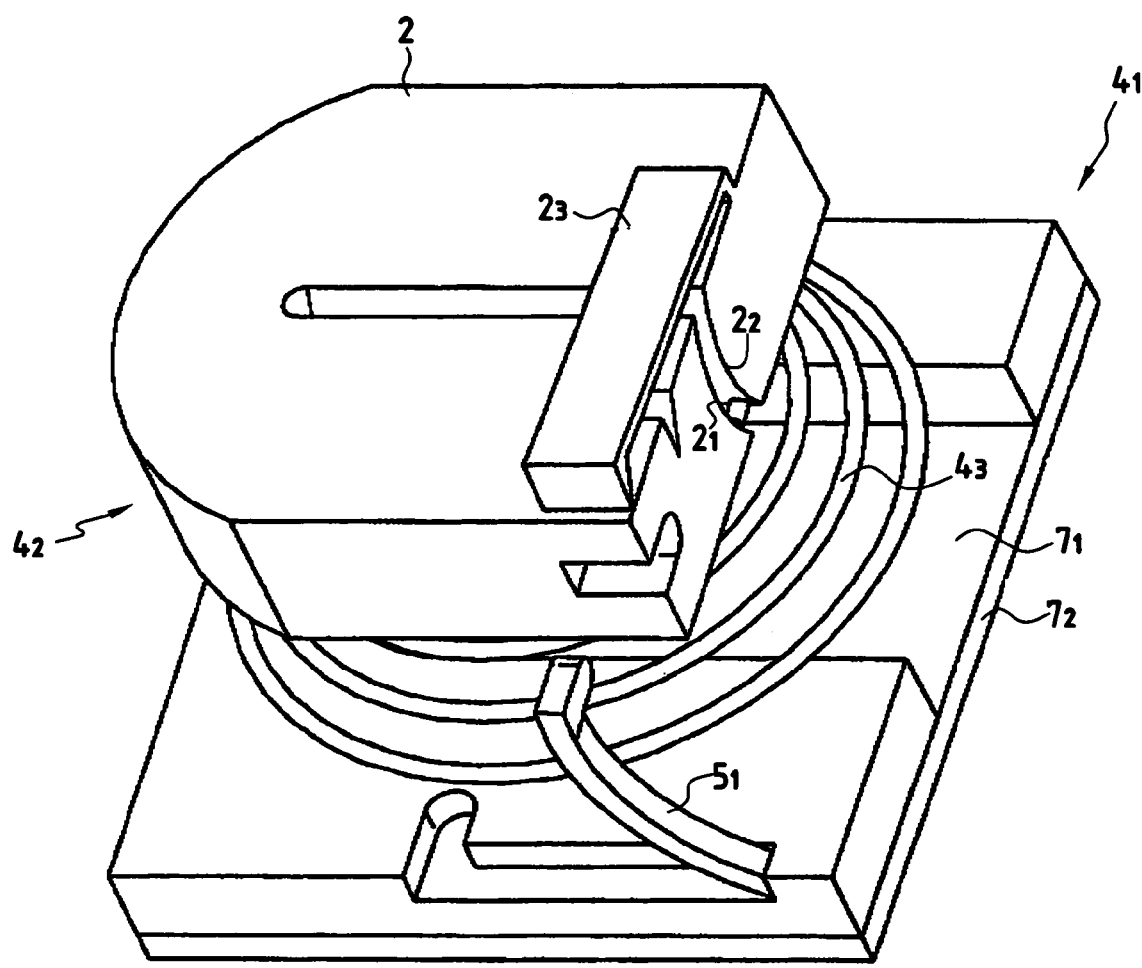
Figure 10:
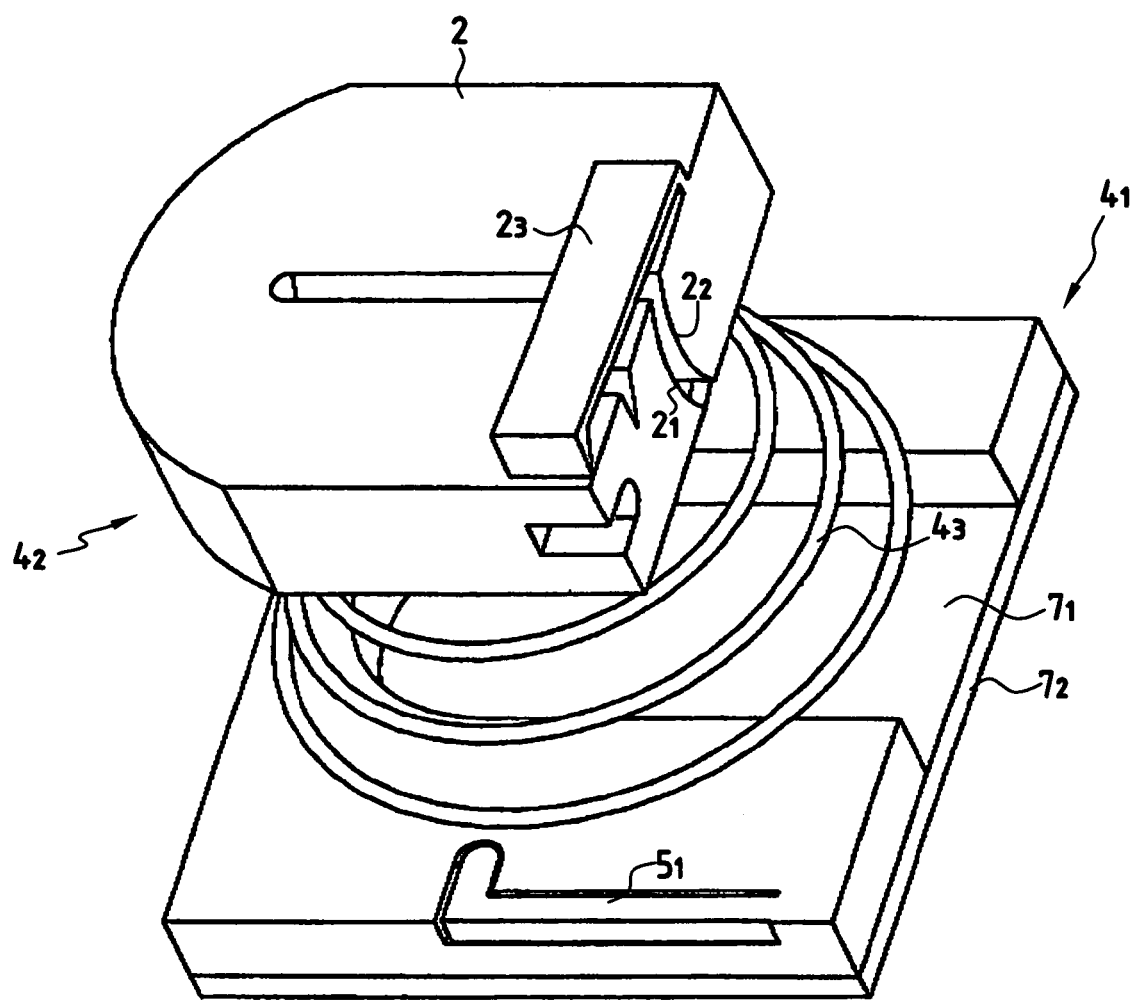

In a second variant embodiment of the invention as shown in FIGS. 8 to 10, the device is constituted by:
a first plate $4_1$ defining a said bearing surface for bearing against said tissue;
a second plate $4_2$ including said blocking zone; and
said first and second plates $4_1$ and $4_2$ are connected together by a resilient junction element comprising a spring blade or wire.

More particularly, a device of the invention comprises:
a said spring wire $4_3$ defining a frustoconical envelope;
said first plate $4_1$ at the end of said spring that corresponds to the large base of said truncated cone formed by the spring;
said second plate $4_2$ at the end of said spring beside the small base of said truncated cone formed by said spring; and
preferably, said spring $4_3$ is suitable for being received in the empty central space thereof when it is compressed by moving said first and second plates towards each other.

It will be understood that in this embodiment, the suture threads pass inside the spring between said first and second plates.

The blocking zone $4_2$ is preferably smaller in size than the contact element $4_1$. In its compressed state, the spring occupies a minimum amount of space in the height direction. The dynamometer behavior is provided by the predefined stiffness of the spring.

This second variant embodiment with a frustoconical spring $4_3$ differs from the U-shaped first embodiment of FIGS. 1 to 4 essentially by the fact that the intermediate junction element $4_3$ is constituted by a said spring $4_3$ of frustoconical envelope.

Otherwise, the blocking zone $4_2$ is likewise constituted by two interconnected jaws. Said blocking zone $4_2$ is constituted by two resiliently-connected jaws 2 that are held spaced apart by a spacer rod $2_3$ secured at one of its ends to one of the two jaws and co-operating at its opposite end with a notch $2_4$ in the second jaw. The two jaws 2 are thus held spaced apart and can thus be held in place on a placing instrument $1_2$. Thereafter, when a bearing force is exerted on the spacer rod $2_3$, it bends and comes out of the notch $2_4$ in the second jaw 2, such that the complementary surfaces $2_1$ and $2_2$ on the two jaws 2 can move towards each other and block the threads (FIG. 9). Simultaneously, the connection rod $5_1$ can become disengaged so that the distance between the first plate $4_1$ and the second plate $4_2$ is then controlled solely by the tension exerted by the connection spring $4_3$. The connecting spring $4_3$ is designed in such a manner that it exerts a tension having a said first value, in particular 2 N, when it goes away said initial distance L between the contact and blocking zones at the time of blocking in order to adopt a said final distance L±b, as explained above.

In this second variant embodiment, the pressure exerted on the ancillary $1_2$ thus causes the suture threads to be blocked together, after which it triggers tensioning of the suture threads once blocked together at a said first predetermined value.

In both variant embodiments shown in FIGS. 1 to 10, the suture device is such that:
at rest, the distance between said contact zone $4_1$ and said blocking zone $4_2$ is equal to L+a;
the distance between said contact zone $4_1$ and said blocking zone $4_2$ is equal to L when the device is in contact with the tissues to be sutured together and in a position ready for blocking, possibly with the device being held in place on its placing instrument (first variant); and
the resilience of the various components of the device, and in particular of the intermediate junction element $4_3$ is designed so that when the distance between said contact zone $4_1$ and said blocking zone $4_2$ lies in the range L−b and L+b (where b<a), a force having said first value, and in particular a value of 2 N, is needed to keep the compressed device at said distance L±b.

By way of illustration, values for L, a and b can be as follows:
L=2 mm, a=1 mm, b=0.5 mm.

Thus, in these two variant embodiments, two situations can arise while the surgeon is putting the suture device into place:

1) First Situation

When blocking is triggered, the tension being exerted by the surgeon on the suture threads is equal to $T_1$ where $T_1<T_0$ ($T_0$=the first predetermined tension value, e.g. 2 N), and the length of the strands of thread between said contact zone and said blocking zone is L.

In this first situation, when tensioning is triggered after blocking has taken place, the device is no longer held by the placing instrument 12 and seeks to expand since it is subjected only to the action of the tension $T_1$ in the threads, so the distance extending between said contact zone $4_1$ and said blocking zone $4_2$ as constituted by the two close-together jaws 2 will take on a value greater than L, i.e. L+b, where b<a. The tension exerted on the suture threads by the device is then equal to $T_0$ and the strands of thread prevent the device from expanding beyond the distance L+b, where <u>b</u> corresponds to the extent to which the threads lengthen under the effect of the difference in tension $T_0-T_1$.

2) Second Situation

When blocking is triggered, the tension exerted by the surgeon on the suture threads immediately prior to blocking is equal to $T_1>T_0$ and the length of the strands of thread between said contact zone and said blocking zone is L.

When, after blocking, tensioning of the threads by the device is triggered, the device will compress under the action of the tension $T_1$ in the threads, and the distance between said contact zone and said blocking zone will take on a value that is less than L, i.e. L−b, where b<a. The tension exerted by the device on the threads is thus equal to $T_0$ and the device prevents the threads from compressing beyond the distance L−b, where <u>b</u> corresponds to the shortening of the strands of thread under the effect of the difference in tension $T_1-T_0$.

Figure 11:
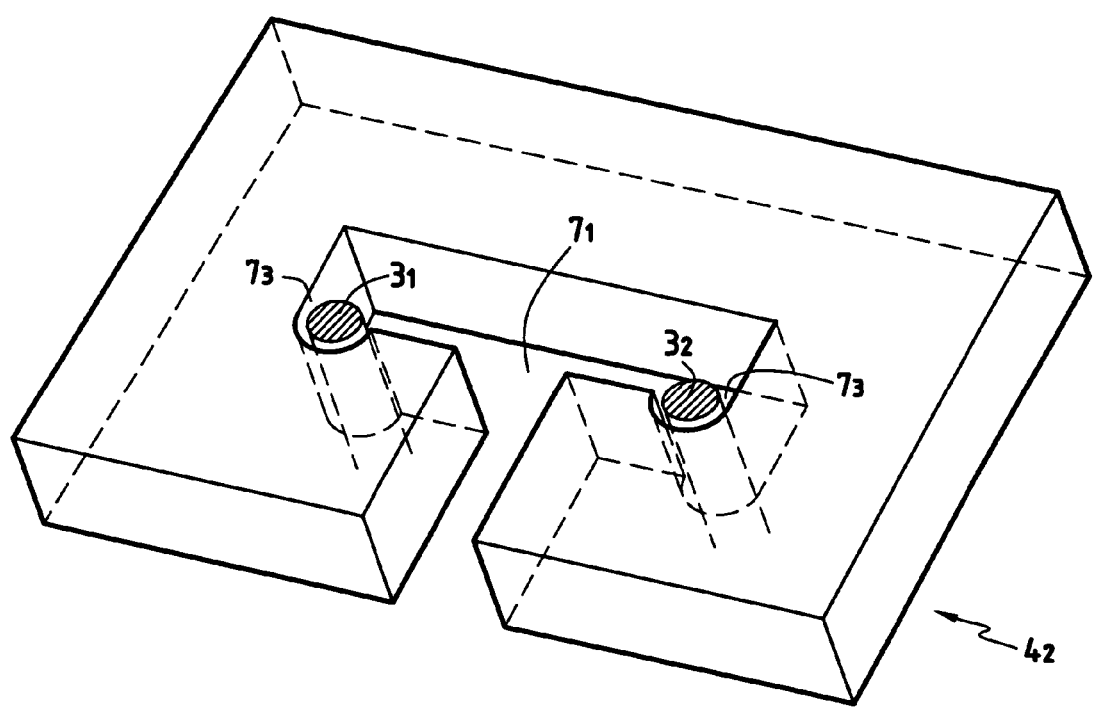
FIG. 11 shows a variant configuration for the notch $7_1$ constituting the guide means in said bearing surface $4_1$.

FIG. 11 shows a variant embodiment of the guide means in said contact zone 1 having a said notch $7_1$ that is in the form of a middle slot on the middle axis of said blocking zone together with two zones $7_3$ that are disposed symmetrically about said middle slot, said two said symmetrical zones $7_3$ comprising or defining retaining abutments for holding the two strands of thread $3_1$ and $3_2$ in a spaced-apart position where they pass through said zones, respectively. Said symmetrical zone $7_3$ of the notch $7_1$ are spaced apart so as to allow the two strands of thread $3_1$ and $3_2$ to be tensioned on the axes of said suture orifices $6_1$, $6_2$ so as to avoid applying any stresses to said suture orifices when exerting tension on the thread.

In the various embodiments, the suture device of the invention when applied to minimally invasive surgery can be put into place, for example, using a placing instrument $1_2$ acting through a trocar having a diameter of 2 mm to 12 mm, said device having a said bearing surface and a said blocking zone which lie within a rectangular area of 2 mm² to 40 mm² and that are spaced apart by a maximum height of 10 mm.

What is claimed is:

1. An implantable device for semiautomatic suturing using a surgical thread, the suturing enabling biological and/or artificial tissues to be united, the device comprising:
   blocking means enabling two strands of the thread of a suture to be connected together in a blocking zone; and
   a bearing element having a bearing surface for bearing against the tissues to be sutured together, said bearing surface comprising a contact zone in which the bearing surface is adapted to be in contact with tissue, and controlled tensioning means for applying controlled tensioning to said thread, and suitable for exerting a tension having a first predetermined tension value independent of tension exerted on the threads before blocking thereof after the two strands of said thread have been blocked together using said blocking means, with the junction between said bearing element and said blocking zone of the device being provided by said controlled tensioning means,
   wherein said controlled tensioning means is constructed and arranged to enable the distance between said blocking zone and said contact zone adapted to be in contact with the tissue to be adjusted after blocking of the strands of thread by the blocking means, between:
   an initial distance in which said two strands of thread can be blocked together; and
   a final distance suitable for exerting said controlled tension having said first predetermined tension value after the blocking,
   wherein said tensioning means comprises resilient junction means between said contact zone and said blocking zone so as to enable the distance between said contact zone and said blocking zone to be adjusted between:
   a controlled initial distance in which the spacing between said contact zone and said blocking zone is controlled by at least one of a first link element and a first spacer element, and said initial distance corresponding to a distance in which said blocking zone and said contact zone are in a close-together position by applying compression compared with a spaced-apart, rest position; and
   said final distance corresponds to a position of force equilibrium in which the distance between said contact zone and said blocking zone is no longer controlled by said at least one of said first link element and said first spacer element.

2. The device according to claim 1, wherein said initial distance between said blocking zone and said contact zone can be obtained using a first link element suitable for initially connecting said blocking zone and said contact zone of the device, and said final distance of said first blocking zone relative to said first contact zone can be implemented by releasing said first link element.

3. The device according to claim 2, wherein said first link element is suitable for co-operating with said blocking means in such a manner that said first link element is released once said strands of thread have been blocked together using said blocking means.

4. The suture device according to claim 1, wherein said device co-operates with a placing instrument to which it is secured, in such a manner that:
   prior to said bearing surface coming into contact with said tissue, said resilient junction means are at rest, and said bearing surface and said blocking zone are in a spaced-apart position;
   when said contact zone is pressed against said tissue for suturing, said resilient junction means is placed in compression and the distance between said contact zone and said blocking zone decreases to said initial distance controlled by said first spacer element, said bearing surface coming into abutment against said first spacer element of said instrument; and
   said final distance is obtained by co-operation between said placing, instrument and said device.

5. The device according to claim 1, wherein the blocking of said strands of thread using said blocking means is constructed and arranged for automatically triggering said tensioning of the threads to said first predetermined tension value.

6. The device according to claim 5, constructed and arranged for the thread to be disengaged so as to be capable of being cut between said blocking zone and suture orifices adapted to be in said tissue, between said blocking zone and said contact zone.

7. The device according to claim 1, which is U-shaped, comprising:
 a bottom first branch defining said bearing surface for bearing against said tissue in use, and including said contact zone;
 a top second branch including said blocking zone and secured with or co-operating with said blocking means; and
 a junction element between said first and second branches, the junction element being made of a semi-rigid material presenting elasticity.

8. The device according to claim 1, which comprises:
 a first plate defining said bearing surface for bearing on said tissue in use, and including said contact zone;
 a second plate including said blocking zone;
 said first and second plates being connected together by a junction element comprising a resilient spring wire or spring blade.

9. The device according to claim 8, wherein:
 said spring wire defines a frustoconical envelope;
 said first plate is placed at the end of said spring beside the large base of said trunctated cone formed by said spring;
 said second plate is placed at the end of said spring that is beside the small base of said truncated cone formed by said spring; and
 said spring is suitable for being received in its own empty central space when it is compressed by moving said first and second plate towards each other.

10. The device according to claim 1, wherein said bearing element, said blocking means, and said controlling tensioning means form a single one-piece mechanical part.

11. An implantable device for semiautomatic suturing using a surgical thread, the suturing enabling biological and/or artificial tissues to be united, the device comprising:
 blocking means enabling two strands of the thread of a suture to be connected together in a blocking zone;
 a bearing element having a bearing surface for bearing against the tissues to be sutured together, said bearing surface comprising a contact zone in which the bearing surface is adapted to be in contact with tissue, and controlled tensioning means for applying controlled tensioning to said thread, and suitable for exerting a tension having a first predetermined tension value independent of tension exerted on the threads before blocking thereof after the two strands of said thread have been blocked together using said blocking means, with the junction between said bearing element and said blocking zone of the device being provided by said controlled tensioning means; and
 guide means enabling the two strands to be held laterally spaced apart from each other at suture orifices adapted to be in said tissue.

12. The device according to claim 11, wherein said guide means comprises at least one notch made in said bearing surface defining said contact zone.

13. The device according to claim 12, wherein said guide means comprises, on an under-face of said notch, a piece of fabric of biocompatible material suitable for being pierced by said two strands of thread in order to keep them spaced apart.

14. An implantable device for semiautomatic suturing using a surgical thread, the suturing enabling biological and/or artificial tissues to be united, the device comprising:
 blocking means enabling two strands of the thread of a suture to be connected together in a blocking zone; and
 a bearing element having a bearing surface for bearing against the tissues to be sutured together, said bearing surface comprising a contact zone in which the bearing surface is adapted to be in contact with tissue, and controlled tensioning means for applying controlled tensioning to said thread, and suitable for exerting a tension having a first predetermined tension value independent of tension exerted on the threads before blocking thereof after the two strands of said thread have been blocked together using said blocking means, with the junction between said bearing element and said blocking zone of the device being provided by said controlled tensioning means,
 wherein said blocking means comprises two blocking surfaces capable of moving between a spaced-apart position in which it is possible to insert said strands of thread between said two blocking surfaces, and suitable for blocking said strands of thread together by friction between the threads and said two blocking surfaces once the surfaces are in a close-together, blocking position, the displacement of said two surfaces between said spaced-apart position and said close-together position automatically triggering said tensioning of the threads after blocking.

15. The device according to claim 14, wherein said blocking of the strands of thread using said blocking means is suitable for being triggered automatically.

16. The device according to claim 15, wherein the automatic triggering of the blocking of said strands of thread using said blocking means take place when the device is pressed into contact with the tissues to be sutured together with a bearing force that is greater than a second predetermined value.

17. The device according to claim 16, wherein the second predetermined value is in a range of 0.2 N to 20 N.

18. The device according to claim 14, wherein said blocking means comprises two jaws resiliently connected together and forming respective blocking surfaces which are held apart by a second spacer element, said second spacer element being suitable for being released by being disengaged or broken so as to enable said blocking surfaces to move towards each other and block said strands of thread together.

19. The device according to claim 18, wherein said second spacer element is suitable for being released automatically.

20. The device according to claim 19, wherein said second spacer element is constructed and arranged for being released automatically by pressing a placing instrument against said second spacer element while said bearing surface of the device is exerting pressure on the tissue in use that is greater than a second determined value of not less than 10 N.

21. The device according to claim 18, wherein said second spacer element is suitable for being released by automatically triggering release of said first link element between said blocking zone and said contact zone of the device so that said zones adopt a said final distance that is adjusted to allow said first controlled tension value to be exerted on said strands of thread.

* * * * *